(12) United States Patent
Stone

(10) Patent No.: US 8,632,475 B2
(45) Date of Patent: Jan. 21, 2014

(54) NON-INVASIVE, BEDSIDE INTRA-CRANIAL PRESSURE AND BRAIN SHIFT/HERNIATION MONITORING UNIT UTILIZING EARLY ONSET AUDITORY EVOKED RESPONSES

(75) Inventor: James L. Stone, Evanston, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 262 days.

(21) Appl. No.: 12/032,384

(22) Filed: Feb. 15, 2008

(65) Prior Publication Data

US 2008/0200832 A1    Aug. 21, 2008

Related U.S. Application Data

(60) Provisional application No. 60/890,116, filed on Feb. 15, 2007.

(51) Int. Cl.
*A61B 5/00* (2006.01)
(52) U.S. Cl.
USPC .......................................... 600/561; 600/559
(58) Field of Classification Search
USPC ......... 600/561, 300, 301, 544, 559, 532, 509, 600/483, 484, 529, 324; 128/200.24; 604/19; 607/116; 702/19
See application file for complete search history.

(56) References Cited

U.S. PATENT DOCUMENTS

| | | | |
|---|---|---|---|
| 5,590,648 A * | 1/1997 | Mitchell et al. | 600/301 |
| 6,974,421 B1 * | 12/2005 | Causevic et al. | 600/561 |
| 2001/0027335 A1 * | 10/2001 | Meyerson et al. | 607/116 |
| 2007/0167694 A1 * | 7/2007 | Causevic et al. | 600/301 |
| 2007/0191688 A1 * | 8/2007 | Lynn | 600/300 |

OTHER PUBLICATIONS

Stone et al, "Modified Auditory Brainstem Responses (MABR): Part I—Rationale and Normative Study", Clinical Electroencephalography, vol. 18, No. 4, 1987.
Stone et al, "Modified Auditory Brainstem Responses (MABR): Part 2—Studies in Patients with Intracranial Lesions", Clinical Electroencephalography, vol. 19, No. 2, 1988.
Nagao, et al., "Prediction and Evaluation of Brainstem Functionby Auditory Brainstem Responses in Patients . . . ", Surgical Neurology, vol. 27, No. 1, Jan. 1, 1987, pp. 81-86.
Jones, et al., "Effects of Temperature and Elevated Intracranial Pressure on Peripheral and Brain Stem Auditory . . . ", Experimental Neurology, vol. 92, No. 1, Apr. 1, 1986, pp. 1-12.
Popovic, "Noninvasive Monitoring of Intracranial Pressure", Recent Patents on Biomedical Engineering 2009, vol. 2, pp. 165-179.

(Continued)

*Primary Examiner* — Brian Szmal
(74) *Attorney, Agent, or Firm* — Michael Best & Friedrich, LLP

(57) ABSTRACT

An intracranial pressure monitoring system and method. The system includes an auditory stimulation and recording unit, which includes a stimulation controller, a memory for storing waveforms, a device for comparing received waveforms with stored waveforms, and an alarm operable based upon that comparison. The system includes at least one cranial electrode attachable to a patient, and an auditory stimulation device, operable by the stimulation controller. The stimulation device is a pair of acoustic ear inserts, each of which is connected to and operated by an auditory stimulator activated by the stimulation controller. In the method, a patient is auditorially stimulated to evoke a received waveform indicative of intracranial pressure, a comparison is generated by comparing the received waveform with one of an established patient baseline waveform and an established normal waveform, and an alarm is generated responsive to that comparison.

9 Claims, 2 Drawing Sheets

(56) References Cited

OTHER PUBLICATIONS

European Patent Office Exam Report for Application No. 08730054.7 dated Mar. 27, 2013 (7 pages).
Hurley et al., "Development of Low-Frequency Tone Burst versus the Click Auditory Brainstem Response," J Am Acad Audio 16:114-121, (2005).
Gorga et al., "Using a Combination of Click- and Tone Burst-Evoked Auditory Brain Stem Response Measurements to Estimate Pure-Tone Thresholds," Ear and Hearing, Williams and Wilkins, US, vol. 27, No. 1, Jan. 1, 2006, pp. 60-74.
Matsuura et al., "Intracranial pressure and auditory evoked responses of the cat", ACTA Otolaryngol., vol. 102, No. 1-2, Jul. 1, 1986, pp. 12-19.

* cited by examiner

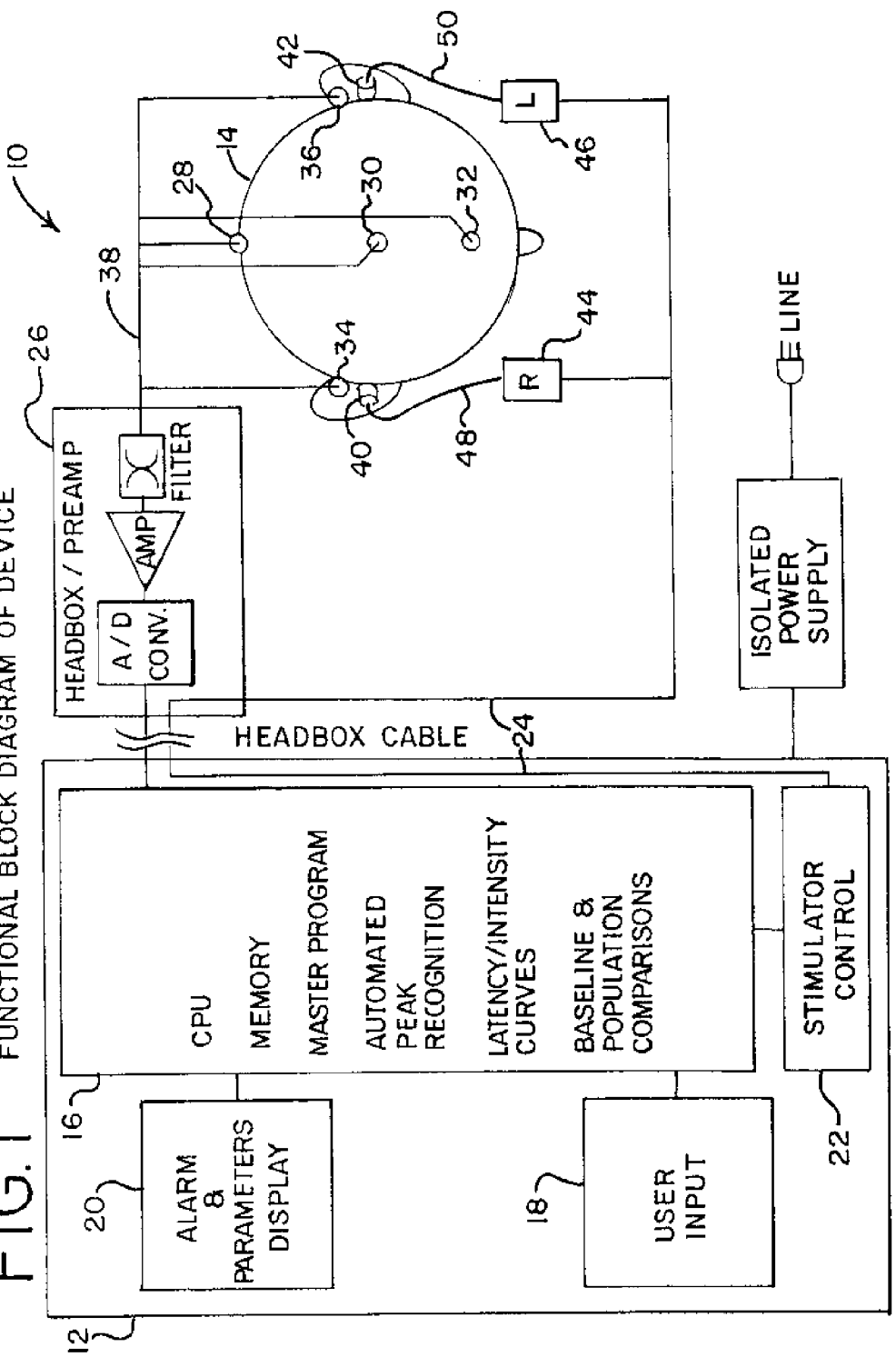

NON-INVASIVE, BEDSIDE INTRA-CRANIAL PRESSURE AND BRAIN SHIFT/HERNIATION MONITORING UNIT UTILIZING EARLY ONSET AUDITORY EVOKED RESPONSES

RELATED APPLICATION

This application is the non-provisional filing of provisional U.S. application Ser. No. 60/890,116 filed Feb. 15, 2007.

BACKGROUND OF THE INVENTION

This invention relates to monitoring intracranial pressure, and in particular to non-invasive intracranial monitoring using waveforms evoked from a patient.

The invention provides a system capable of monitoring intra-cranial pressure (ICP), using early onset auditory brainstem response (ABR), modified auditory brainstem response (MABR) and electrocochleography (ECochG) methods. The invention is used to estimate when ICP is increased, or has increased compared to the patient's earlier baseline value. This nurse-friendly, monitoring and warning system constitutes an important bedside surveillance system for a high risk patient group. It is fully automated in both the presentation of auditory stimuli and immediate analysis of the recorded potentials—not requiring that a neurologist, neurosurgeon or neurophysiologist be present for the test or its interpretation.

Increased ICP is commonly seen in conditions such as brain tumors, head injury, stroke, or cerebral fluid (CSF) build up in hydrocephalus. The management of increased intra-cranial pressure remains a major obstacle to the successful treatment of many patients with life-threatening intra-cranial space-taking lesions. At the present time, the measurement of ICP requires an invasive procedure—a hole must be drilled through the skull and often the cerebrum must be punctured. Various medical or surgical measures may be used to alleviate increased ICP if detected in a timely fashion. Patients with headaches or certain findings on clinical examination such as drowsiness or focal neurological signs or brain scans that suggest increased ICP, are usually seen in an emergency room and closely observed in the intensive care unit (ICU) Unfortunately, even today, patients with brain masses may rapidly deteriorate as lesions enlarge, and the urgency of surgical or medical measures to combat increased ICP can be misjudged. Nurses and physicians may be short staffed or busy with other patients, and neurological status may be clouded by sedative medications given for headache or restlessness.

It has been known for many years that increased ICP is frequently associated with fullness in the ears, mild or moderate usually low tone hearing impairment, and dizziness or imbalance. The cause is likely related to the cochlear aqueduct, a distinct channel in the basal skull that interfaces CSF with perilymph destined for the cochlea. Animal studies bear out direct increased CSF/ICP pressure transmission to the inner ear and associated damping of electrocochleography (EcochG) potentials. EcochG has not previously been used in patients with increased ICP. Some comparison has been made to Meniere's disease or 'endolymphatic hydrops—typified by episodic symptoms of vertigo, progressive sensorineural hearing loss tinnitus, and fullness in the ear—with disturbed EcochG potentials recorded from symptomatic patients.

Early-onset or short latency auditory evoked responses (ECochG, ABR, MABR) are robust, reliably recorded potentials largely refractory to the presence of depressant and anesthetic medications or the patient's level of consciousness—making these responses an ideal choice in the intensive care setting. Wave V—the most prominent waveform of the ABR and MABR, and the chosen target for automated analysis, is generated from the critical midbrain region of the brainstem. This same region is highly vulnerable to the effects of transtentorial brain herniation, the most common and fatal form of deterioration in patients with intracranial mass lesions and increased ICP. Thus the ABR and MABR Wave V can capture the early phases of this devastating deterioration associated with increasing ICP.

Many studies have demonstrated abnormalities in the conventional or standard click-evoked auditory brainstem response (ABR) in patients with increased ICP, and reversal of these abnormalities with normalization of ICP. The standard ABR is well known to be sensitive to brainstem lesions or compression, as found in later stages of increased ICP. However, the invention mirrors rises in ICP compared to a patient's earlier baseline, and captures mild or moderate increases in ICP, and also the late stages of actual brainstem shift.

Published reviews in this field have yielded the knowledge that the conventional or routine-click evoked ABR, without actual midbrain shift, may reflect moderately increased ICP in less than one-half of patients, but often with only non-specific abnormalities. This led the present inventor to develop the MABR to further challenge the cochlea yet keep the test practical and require minimal time. However, the results of these studies could not be accessed in a timely manner, as required to be useful to a critically ill patient under observation, and necessitated a neurologically trained physician or clinical neurophysiologist to interpret the results. Ordinarily, evoked potential studies require such a professional for interpretation.

SUMMARY OF THE INVENTION

The invention is a user-friendly automated system that samples and automatically analyzes early auditory responses, and produces a timely warning signal to alert nursing staff or others of changes reflecting increased ICP. In one form of the invention, it is directed to an intracranial pressure monitoring system, comprising an auditory stimulation and recording unit, which includes a stimulation controller, a memory for storing at least one of established patient baseline waveform data and normative range waveform data, a device for generating a comparison by comparing received waveform data with established patient baseline waveform data or normative range waveform data, and an alarm which is operable based upon that comparison.

At least one cranial electrode is provided, which is attachable to a patient. An audible stimulation device is included, operable by the stimulation controls.

In accordance with the preferred form of the invention, the auditory stimulation device includes at least one ear stimulation instrument and an auditory stimulator connected to the ear stimulation instrument. Preferably, there is a pair of ear stimulation instruments, and each ear stimulation instrument comprises an acoustic ear insert.

Preferably there is a plurality of the cranial electrodes, for judicious placement cranially on a patient. Between three and five electrodes may be used.

The alarm may be audible, visual or a combination of audible and visual.

The method according to the invention comprises the steps of auditorially stimulating a patient to evoke a received waveform data indicative of intracranial pressure, then generating a comparison by comparing the received waveform data with one of established patient baseline waveform data and established normative waveform range data, and, finally, generating an alarm responsive to that comparison.

BRIEF DESCRIPTION OF THE DRAWINGS

The invention is described in greater detail in the following description of examples embodying the best mode of the invention, taken in conjunction with the drawing figures, in which:

FIG. 1 is a block diagram of a system according to the invention.

DESCRIPTION OF EXAMPLES EMBODYING THE BEST MODE OF THE INVENTION

Figure 3:
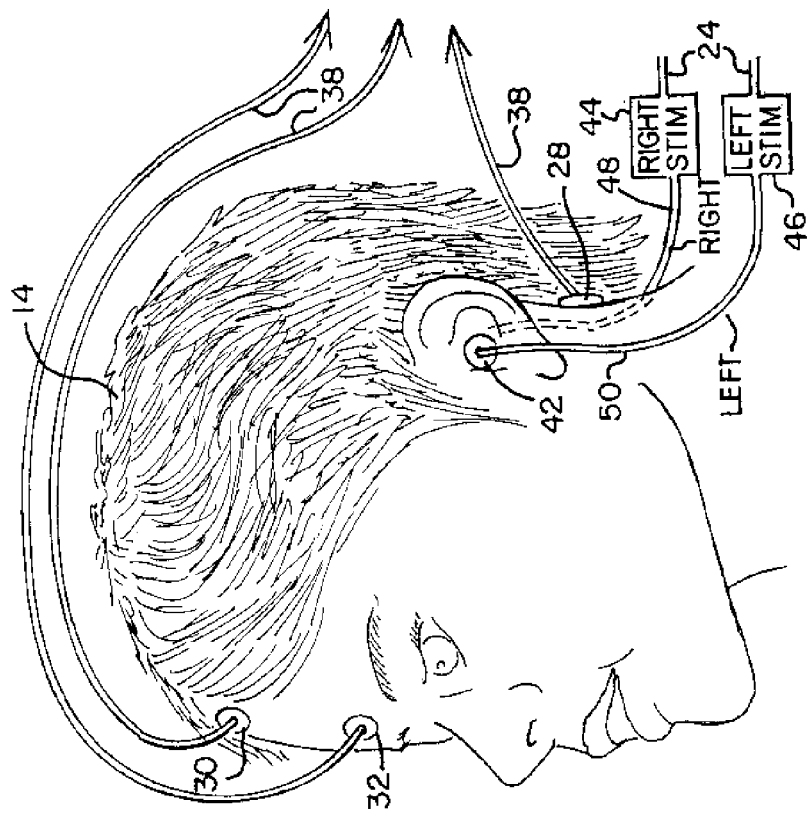
FIG. 3 illustrates use of the invention with MABR.

Patients would greatly benefit if a safe, non-invasive bed-side method existed to automatically sample and interpret physiologic signals that reflect increasing ICP in a timely manner. The system of the invention is used to monitor ICP utilizes MABR or/and EcochG methodology, and is not significantly affected by patients taking depressant or paralytic medications, or under general anesthesia. The system should greatly impact patient care, save lives, and lead to fewer invasive ICP monitoring procedures. The system should be a valuable back-up safety measure to existing medical and surgical management, including invasive ICP monitors which can fail about 7% of the time.

As explained in greater detail below, the invention may utilize conventional components, such as Bio-logic (Natus/Bio-logic, Mundelein, Ill.) instrumentation and accessories. A commercially available Navigator Pro laptop based unit can be used to perform stimulation, recording, amplification, averaging, and display of waveforms. A separate component stimulator and preamplifier is attached directly to the patient. Auditory stimulation is delivered by soft foam ER 3A insert headphones placed just within the external ear canal, and all recordings by noninvasive skin surface stick-on or gel electrodes. A Biologic TM (tympanic membrane) electrode is exclusively used for ECochG. Natus/Bio-logic is additionally a leader in the manufacture and distribution of automated, nurse friendly ABR devices used routinely world-wide as a hearing screen in neonates.

Electrocochleography (ECochG)—Analysis of electrical signals generated by the cochlea which—require proximity to the inner ear to be reliably recorded following moderately loud (100-105 dBpeSPL) auditory click stimulation delivered by insert headphones. An adequate eighth nerve action potential (AP) voltage of about 1 microvolt (uV) is recorded from the tympanic membrane (TM) electrode referred to the contralateral mastoid skin surface (nasion ground) with a latency of about 1.5 millisecond after the auditory stimulation. In addition to the AP, are two earlier cochlear hair-cell receptor potentials whose onset begins with the auditory stimulation—the cochlear microphonic (CM), and summating postential (SP).

Auditory Brainstem Response (ABR)—consists of five positive vertex scalp recorded waves generated by the auditory nerve and 4 auditory brainstem nucleii or tracts, recorded within 6 to 7 milliseconds. Foam insert headphones deliver a moderately loud (100-105 dBpeSPL) auditory click stimulus at approximate rates between 11-22 per second. Wave V (and following Vn) are usually most prominent with a voltage (amplitude) approaching ½ microvolt (uV). For ABR the active skin surface electrode is placed at the frontal vertex (Fz) and referenced at the ipsilateral mastoid skin surface. A surface ground electrode is placed at the nasion. The ABR, most notably Wave V, can also be generated by an insert headphone that delivers a pure tone burst stimulus, and is recorded with identically placed recording electrodes. In some instances, this tonal ABR may have more promise than the conventional click ABR in capturing ICP.

Modified Auditory Brainstem Response (MABR)—is elicited by a rapid click stimulation rate of about 40-70 per second and binaural (bilateral simultaneous) presentation to both ears, both modifications augment the amplitude of the prominent Wave V (and Vn) which are the major waveforms of interest. The frontal vertex (Fz) referred to C2 neck linkage also augments Wave V amplitude. A ground is placed at the nasion. This augmentation is necessary since the MABR is performed at 4 moderate loudness intensities (i.e. 85, 75, 72, 65 dBpeSPL), all well below that of the standard ABR (100-105 dBpeSPL). These maneuvers stress the cochlea, yet yield a robust Wave V (approximately 1 uV) for automated Wave V recognition, Wave V latency/intensity and Wave V amplitude/intensity curves for analysis, display if desired, and warning. An MABR wave V (and Vn) can also be generated by a pure tone This invention is for a bed-side auditory stimulation and surface scalp recording device that can use tympanic membrane recorded electrocochleography (ECochG), the conventional click-evoked, or pure tone burst auditory brainstem response (ABR), and modified click or tone burst evoked ABR (MABR) tests involving bilateral (binaural) or unilateral-rapid stimulation rates of diminishing stimulation intensities to create Wave V latency/intensity and Wave V amplitude/intensity decay curves. Easily tolerated soft foam insert headphones deliver the stimuli and simple skin surface electrodes are used for recording the potentials. Wave V, the most prominent ABR waveform, can be windowed and captured (peak picking) with software facilitating automated wave form recognition and analysis. Software can also handle waveforms derived at diminishing intensities and create the above mentioned latency/intensity and amplitude/intensity curves. When these curves reach critical values compared to an earlier baseline in the same patient or curves derived from normals, a warning tone and light alerts hospital staff of the concern for increasing ICP in the patient. The early-onset evoked response battery can be automatically set to be administered every 10 or 20 minutes (etc), as determined by the nursing staff or physicians.

A non-invasive, bedside intra-cranial pressure monitoring system 10 according to the invention is generally illustrated in block form in FIG. 1. The system 10 includes an auditory stimulation and recording unit 12 which may, as explained below, be a single unit or a series of individual elements joined as a unit. The auditory stimulation and recording unit 12 is used for monitoring the ICP of a patient 14, as also explained further below.

The auditory stimulation and recording unit 12 includes a CPU 16, which may be a general purpose computer, as identified above, and which includes all software and memory needed in order to perform not only storage of waveform data, but also analysis required by the invention. The CPU 16 thus includes, as indicated on the CPU 16, memory, the master program necessary for operation, automated peak recognition for analyzing waveform data received from the patient 14, latency/intensity curves which provide normative range waveform data, and baseline and population comparisons. The baseline can include patient baseline waveform data collected from the patient 14, and the population comparisons can include waveform data gathered from patients with known levels of increased ICP. A user input 18, which may be as simple as a keyboard, is used to import data into the CPU 16.

The unit 12 also includes alarm and parameters display 20. The display 20 can be as simple as an audible alarm, or a visual display, or a combination of both audible and visual displays to provide an indication relative to comparison of waveform data received from the patient 14 with data stored in the CPU 16.

The unit 12 also includes a stimulator control 22. The stimulator control 22 is used to send stimulating signals to the patient 14 via a cable 24, or wirelessly if wireless connections are used.

For appropriate connection to electrodes placed on the patient 14, the auditory stimulation and recording unit 12 is connected through a typical preamplifier 26. Depending on the system being used to obtain waveform data from the patient 14, electrodes 28 through 36, which may be non-invasive skin surface stick on or gel electrodes, are employed. The electrodes 28 through 36 are connected via cables 38 to the preamplifier 26 and then to the auditory stimulation and recording unit 12.

For auditory stimulation, ear inserts 40 and 42 are used. The inserts 40 and 42 may be standard soft foam insert headphones which are placed just within the external ear canal of the patient 14. Each of the ear inserts 40 and 42 is activated by a respective conventional auditory stimulator 44 and 46 through a respective acoustic tube 48 and 50.

Figure 2:
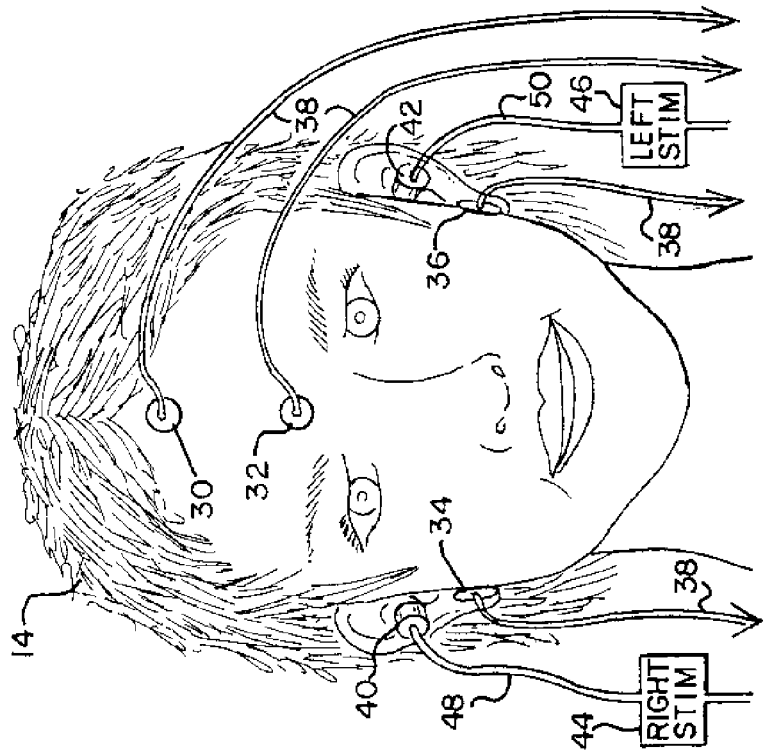
FIG. 2 is an example of use of the invention with ABR click or pure tone.

FIG. 2 illustrates the invention, using auditory brainstem response (ABR). For this purpose, the electrode 30 is placed at the frontal vertex and the electrode 32 is placed at the nasion as a surface ground electrode. The electrodes 34 and 36 are mastoid electrodes from which waveform data may also be obtained.

FIG. 3 illustrates the use of the invention with MABR. The electrode 30 is connected to the frontal vertex and the electrode 32 is connected at the nasion as a ground. The electrode 28 is connected at the neck to augment the wave V amplitude.

Initiation of an alarm at the display 20 depends on set limits that are set in the unit 12. Intensive care unit monitoring of early-onset (short latency) auditory evoked responses is similar to intra-operative monitoring, and if there is a frifty percent drop in the wave V amplitude, or ten percent increase in wave V latency, compared to the patient's baseline waveform data, the CPU 16 can be set to issue a warning via the display 20. Other limits can also be set, such as a wave V latency shift or wave V amplitude drop beyond 2.5 standard deviations can trigger a warning by the display 20.

While the invention has been described with respect to comparison of patient waveform data with either the patient's baseline waveform data or normative range waveform data, it can also be compared with other waveform data, such as waveform data from a group of patients with known levels of increased ICP.

Even more rapid rates of auditory stimulation (100 or more clicks or tone bursts per second—requiring maximum-length sequence techniques) may bring out first and higher order nonlinear responses, which may prove more sensitive to changes in ICP. A stimulator and preamplifier component may be attached directly to the patient, held by a neck band or pocket, and this portable component (the size of a deck of cards) communicating wirelessly with the near-by bedside unit 12. The patient could return from tests without a need to remove the electrodes or ear inserts, and once again be within range of the base unit for monitoring.

Various changes can be made to the invention without departing from the spirit thereof or scope of the following claims.

What is claimed is:

1. An intracranial pressure monitoring system, comprising
   a. an auditory stimulation and recording unit, including
      i. a stimulation controller configured to evoke and augment patient waveform data comprising at least one of Wave V and Wave $V_n$,
      ii. a non-transitory memory, said memory including means for storing at least one of established patient baseline waveform data and normative range waveform data,
      iii. a comparing device, said comparing device including means for generating a comparison by comparing the patient waveform data with established patient baseline waveform data or normative range waveform data in a timely manner,
      iv. an alarm, said alarm being operable based on said comparison, said alarm being configured to be generated only when said comparison exceeds a threshold,
   b. at least one cranial electrode adapted to be non-invasively attachable to a patient and receive the patient waveform data from the patient,
   c. an auditory stimulation device, separate from said cranial electrode, said auditory stimulation device being adapted to be connected to a patient and being operable by said stimulation controller to generate said patient waveform data, said stimulation device configured to generate at least one of a pure tone stimulus and a click stimulus, and
   d. said waveform data corresponding to intracranial pressure.

2. The intracranial pressure monitoring system according to claim 1, in which said auditory stimulation device comprises
   a. at least one ear stimulation instrument, and
   b. an auditory stimulator connected to said ear stimulation instrument.

3. The intracranial pressure monitoring system according to claim 2, including a pair of ear stimulation instruments.

4. The intracranial pressure monitoring system according to claim 3, in which each ear stimulation instrument comprises an acoustic ear insert.

5. The intracranial pressure monitoring system according to claim 1, including a plurality of said cranial electrodes.

6. The intracranial pressure monitoring system according to claim 1, in which said alarm is an audible alarm.

7. The intracranial pressure monitoring system according to claim 1, in which said alarm is a visual alarm.

8. The intracranial pressure monitoring system according to claim 1, in which said alarm is audible and visual.

9. A method of monitoring intracranial pressure, comprising the steps of
   a. auditorially stimulating a patient at a first location with at least one of a pure tone stimulus and a click stimulus to evoke and augment patient waveform data comprising at least one of Wave V and Wave $V_n$,
   b. receiving the patient waveform data at a second location on a patient's head, separate from said first location,
   c. generating a comparison by comparing the received patient waveform data with one of established patient baseline waveform data and established normative range waveform data, and d. generating an alarm responsive to said comparison, said alarm being generated only when said comparison exceeds a threshold.

* * * * *